(12) United States Patent  (10) Patent No.: US 8,328,691 B2
Lanfermann et al.  (45) Date of Patent: Dec. 11, 2012

(54) FEEDBACK DEVICE FOR GUIDING AND SUPERVISING PHYSICAL EXCERCISES

(75) Inventors: Gerd Lanfermann, Aachen (DE); Richard Daniel Willmann, Siegburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 665 days.

(21) Appl. No.: 12/526,562

(22) PCT Filed: Feb. 7, 2008

(86) PCT No.: PCT/IB2008/050434
§ 371 (c)(1),
(2), (4) Date: Aug. 10, 2009

(87) PCT Pub. No.: WO2008/099301
PCT Pub. Date: Aug. 21, 2008

(65) Prior Publication Data
US 2010/0022351 A1    Jan. 28, 2010

(30) Foreign Application Priority Data
Feb. 14, 2007  (EP) ..................................... 07102371

(51) Int. Cl.
*A63B 71/00* (2006.01)
(52) U.S. Cl. .................................. 482/1; 482/9; 482/901
(58) Field of Classification Search .................. 482/1–9, 482/900–902; 434/247, 257; 463/31–34; 473/156, 267
See application file for complete search history.

(56) References Cited

U.S. PATENT DOCUMENTS

| | | |
|---|---|---|
| 3,353,282 A | 11/1967 | Sneed |
| 4,337,049 A | 6/1982 | Connelly |
| 4,757,453 A | 7/1988 | Nasiff |
| 5,249,967 A | 10/1993 | O'Leary et al. |
| 5,342,054 A * | 8/1994 | Chang et al. ................... 473/156 |
| 5,375,610 A | 12/1994 | LaCourse et al. |
| 5,913,727 A | 6/1999 | Ahdoot |
| 6,231,527 B1 | 5/2001 | Sol |
| 6,387,061 B1 | 5/2002 | Nitto |
| 6,834,436 B2 | 12/2004 | Townsend et al. |
| 7,018,211 B1 * | 3/2006 | Birkholzer et al. ............ 434/257 |
| 7,679,689 B2 * | 3/2010 | Kitaura ......................... 348/734 |
| 7,952,537 B2 * | 5/2011 | Allen et al. ...................... 345/32 |
| 7,959,511 B2 * | 6/2011 | Kouno ............................. 463/31 |
| 2003/0112147 A1 | 6/2003 | George et al. |
| 2010/0062869 A1 * | 3/2010 | Chung et al. ................... 473/131 |

FOREIGN PATENT DOCUMENTS

| | | |
|---|---|---|
| EP | 0074231 A2 | 3/1983 |
| WO | 0077604 A2 | 12/2000 |
| WO | 2005031552 A2 | 4/2005 |
| WO | 2007000743 A2 | 1/2007 |

OTHER PUBLICATIONS

Lozano et al: "VR-Mirror: A Virtual Reality System for Mental Practice in Post-Stroke Rehabilitation"; LNCS 3638, Springer-Verlag 2005, A. Butz et al. (Eds.), pp. 241-251.

(Continued)

*Primary Examiner* — Glenn Richman

(57) ABSTRACT

A feedback device for guiding and supervising physical exercises includes a compuputer devide having a CPU and a memory, a mirror display device includes a display device having a reflective surface, and position-sensing device for a person disposed before the device.

13 Claims, 2 Drawing Sheets

OTHER PUBLICATIONS

Sathian et al: "Doing It With Mirrors: A Case Study of a Novel Approach to Neurorehabilitiation"; Neurorehabilitation and Neural Repair 2000, Demos Medical Publishing, vol. 14, No. 1, 2000, pp. 73-76.

Kuhn et al: "Interaction of Vision and Movement Via a Mirror"; Perception, 2005, vol. 34, pp. 1153-1161.

Ramachandran et al: "Synaesthesia in Phantom Limbs Induced With Mirrors"; Proc. Royal Society of London B (1996), vol. 263, pp. 377-386.

Lee et al: "Using Biofeedback for Standing-Steadiness, Weight-Bearing Training"; IEEE Engineering in Medicine and Biology, Nov./Dec. 1996, pp. 112-116.

Holmes T Al: "When Mirrors Lie: 'Visual Capture' of Arm Position Impairs Reaching Performance"; Cognitive, Affective & Behavioral Neuroscience 2004, vol. 4, Issue 2, pp. 193-200.

\* cited by examiner

FEEDBACK DEVICE FOR GUIDING AND SUPERVISING PHYSICAL EXCERCISES

FIELD OF THE INVENTION

The present invention is related to a feedback device for guiding and supervising physical exercises, in particular home rehabilitation exercises.

BACKGROUND OF THE INVENTION

Stroke is the most prominent cause of permanent disability in industrialized countries. Motor disabilities are the most common deficits after stroke. Rehabilitation exercises are proven to be efficient to regain motor control, provided the training is intense, the patient is guided in the therapy and receives adequate feedback.

Recently, training devices for unsupervised home use have been introduced. These devices work without a therapist, which means that, once a patient has been introduced to the device, the patient may carry out rehabilitation exercises more frequently, which again increases and accelerates his recovery.

Technical solutions for unsupervised home stroke rehabilitation require the use of sensors for acquiring the patient's posture during exercises. These sensors can be either inertial sensors such as the popular MT9 sensor provided by XSENS, or camera-based Systems such as e.g. the Opti Track system manufactured by Natural Point, respectively.

In both devices, the patient's movements are recorded, compared to a template posture and/or movement and the difference is then reported to the patient in a suitable way. The Core:Tx system manufactured by Performance Health uses a rendered human-like figure for displaying the template posture and/or movement that the patient is supposed to perform. The patient wears an inertial sensor on the affected limb. His own movement is not displayed on screen. A green or red light indicates agreement or disagreement of template and patient movement. These devices are for example described in U.S. Pat. No. 6,834,436.

Displaying the difference between the provided template and the patient's movement is crucial for the effectiveness of a home rehabilitation system, as stroke victims are often not aware of their deficits and show genuine surprise that their performance does not reflect the movement templates.

The existing approaches to home rehabilitation, as for example described in U.S. Pat. No. 6,231,527, use feedback systems that the user finds difficult to get acquainted with. Existing systems use a rendered figure for displaying the patient's movement. It is difficult for the user to identify himself with such a rendered figure. However, as mentioned above, perceiving one's own movement as being not according to the template is a crucial step on the road to recovery for this patient group.

Furthermore, existing Systems use a Computer screen for displaying feedback. However, stroke victims are mostly elderly persons that are not acquainted with Computers. Therefore it is desirable to use a feedback device that provides advantages in terms of ease of use, intuitivity of use, and efficiency of use, especially for elderly people.

SUMMARY OF THE INVENTION

It is an object of the present invention to provide a feedback device for guiding and supervising physical exercises, in particular home rehabilitation exercises, which avoids the above identified shortcomings. It is another object of the present invention to provide such a feedback device which is easy to use especially for elderly people.

Yet another object of the present invention is to provide such a feedback device which gives the patient the possibility to observe his own movements, and/or which makes it easy for the patient to identify himself with a computer-generated animation that displays the patient's movement.

This object is achieved by a device and/or a method according to the independent claims. The dependent claims indicate preferred embodiments. In this context it is noteworthy to mention that all ranges given in the following are to be understood to include the values defining these ranges.

According to the invention, a feedback device for guiding and supervising physical exercises, in particular home rehabilitation exercises of a person, is provided. The device comprises
a) a computer device having a CPU and a memory,
b) a mirror display device comprising a conventional display device having a reflective surface, and
c) position-sensing means for a person disposed before the device.

Said person is for example a patient that undergoes home rehabilitation exercises. However, in the following, the terms "patient" and person" will be used synonymously, i.e. that all considerations related to a "patient" will also be applicable to a "person", and vice versa.

The term "conventional display device", as used herein, relates to a device which is capable of displaying a computer-generated animation. Such displays are well known to the skilled person, and may be selected from CRT (Cathode Ray Tubes), LCD (Liquid Crystal Displays) and the like.

The term "mirror display device", as used herein, refers to a combination of a mirror function and a display function. For example, such a device may comprise a combination of a semi-transparent mirror with a flatscreen monitor. In another embodiment, the device may consist of a flatscreen monitor having a front screen which is coated with a semi-transparent coating.

In a preferred embodiment of the present invention it is provided that the device comprises means for controlling the transmission and/or reflectance of the reflective surface. Such a device may, in a preferred embodiment, consist of a flatscreen monitor, like an LCD, the panel of which is coated with a polarizing film that adjusts the whole, or a portion, of its surface so as to be either transmissive, reflective, or semi-reflective. By this means, the mirror display device can either display computer-generated animations, or it can (passively) display the mirrored image of an object disposed before the display, or it can display both at the same time. Such a product has recently been developed and protected with IP rights by the applicant, and it is being marketed under the trademark "Mirror TV".

The term "computer-generated animation", as used herein, refers to both still images and animated images. In said device, the body posture of the person standing before the mirror is first detected by the position-sensing means, and then an image is generated and displayed which is overlaid over the person's mirror image.

Then, a predetermined body posture or movement (in the following called: "template posture and/or movement") is displayed, which the person can perceive and is then supposed to perform.

Upon performing the posture or movement, the person will immediately perceive any deviations between the template posture or movement and his own posture or movement by comparing the computer-generated animation and his own mirrored image, and will thus receive feedback which enables him to correct his posture or movement.

Moreover, position-sensing may be used to detect deviations between the template posture and/or movement and the movements carried out by the person. These deviations can be reported to the person in real time by displaying them in an educative fashion on the display, or by creation of a warning sound, in order to tell the person whether or not he has correctly performed the template posture and/or movements. In addition thereto, the person can figure out deviations between the template posture and/or movements and his own movements by comparing the computer-generated animation and his own mirrored image. The person will thus be able to correct his movements on the basis of the above feedback information. The information is provided in such a way that it is perceived intuitively, so that the person may pick up the information while concentrating on the exercises.

By these means, an easy-to-use real-time feedback device is accomplished, which helps persons suffering from post-stroke motor disabilities to carry out therapeutic rehabilitation exercises which are proven to be efficient to regain motor control, provided the training is intense, the person is guided in the therapy and receives adequate feedback. The system is particularly suited for home use. This means a person can carry out therapeutic rehabilitation exercises without supervision by a therapist, which means that exercise frequency and/or intensity can be substantially increased, which results in a better and faster rehabilitation.

In a preferred embodiment of the present invention, it is provided that the device comprises means for generating an animation of the person, based on data provided by the position-sensing means, and displaying said animation on the mirror display device in such a way that the displayed animation and a reflected image of the person are overlaid, one on top of the other.

Again, the term "animation", as used herein, refers to both still images and animated images. The person is thus enabled to directly compare the template posture or movements to his own body posture or movements. This feature enhances the intuitive information uptake by the person and does thus contribute to a better concentration on the exercises which the person is supposed to carry out, and will consequently support the rehabilitation process.

In another preferred embodiment of the present invention, it is provided that the position-sensing means for the person comprises either body-worn sensors or markers, and/or a camera system.

These sensors or markers can be inertial sensors such as MEMS (Micro-Electro-Mechanical System) sensors (commonly known as movement trackers), which are for example used in movie animation, training sciences and the like, and which are for example supplied by the company Xsens movement technologies. These embodiments can be collectively referred to as "active sensors or markers".

Likewise, optical markers comprising colours can be used. In a preferred embodiment, the markers comprise means which are fluorescent or detectable under infrared illumination. These embodiments can be collectively referred to as "passive sensors or markers".

Camera-based systems may for example consist of a camera mounted in the frame of the mirror display device, which creates recordings of the person's body movements, which will then form the basis for the later analyses and image generation processes.

In a preferred embodiment, the position-sensing means for the person comprises both body-worn sensors or markers and a camera system. In this case, the markers comprise detectable devices (i.e. IR-LED or the like) which are detected by the camera in order to precisely determine the positions of the limbs etc. Such devices are for example supplied by the company Natural Point.

In another preferred embodiment, the camera system is a stereo camera system. In this case, dedicated body-worn sensors or markers are not necessary, as the camera system can calculate the positions of the person's limbs by analyzing the stereo images. However, even in such a system the detection of the person's body will be easier if the latter is equipped with body-worn sensors or markers.

Furthermore, a feedback method for guiding and supervising physical exercises, in particular home rehabilitation exercises of a person, is provided. Said method comprises the steps of a) disposing a person before a feedback device comprising: a CPU and a memory, a mirror display device comprising a conventional display device having a reflective surface, and position-sensing means for the person, b) detecting the person's body posture and/or body movements, and c) generating and displaying a computer-generated animation on the mirror display device, which represents a template posture and/or movement.

In this embodiment, the CPU memory contains predetermined template postures and movements which the person is supposed to perform.

In a preferred embodiment of this method, the method further comprises detecting any deviations between the template posture and/or movement and the person's body posture and/or body movements.

This means that the person's body posture and/or body movements are monitored throughout the exercise. Any deviations detected can then be reported to the person in order to generate feedback information according to said deviation. The feedback information may for example consist of a dotted line on the mirror display device, which symbolizes the limb deviating in its posture from the template posture (see FIG. 1). Feedback information can also be presented in the form of an audible signal. The person skilled in the art can easily select other feedback information channels and/or devices, and these fall under the scope of the present invention as well.

In a preferred embodiment of the method according to the invention, a feedback device according to the invention is used for carrying out said method.

In yet another preferred embodiment of the method according to the invention it is provided that the method comprises the execution of an algorithm selected from the group consisting of:

a) an algorithm to detect the 3D positions of the person and his limbs when disposed before the mirror display device, b) an algorithm to compute the coordinates of the mirror image of the person and/or his limbs on the surface of the mirror display, c) an algorithm for creating a computer-generated image of a figure the limbs of which appear at the same points on the surface of the mirror display as in the mirror image, as computed by the algorithm mentioned in point b), d) an algorithm to animate the computer-generated image according to the template posture and/or movement, and/or e) an algorithm to generate feedback information according to the deviation of the person's posture and/or movement from the template posture and/or movement.

The term "posture" herein refers to the positions and orientations of the person's limbs, his head, his backbone and other parts of his body.

Furthermore, a method for carrying out, guiding and/or supervising physical exercises and movements is provided, comprising procedural steps according to the above described feedback method. It is to be understood that such a method provides the advantages set forth hereinabove in connection with the feedback device and the feedback method.

Furthermore, the use of a system according to the invention for carrying out, guiding and supervising exercises is provided. Such exercises can for example belong to the field of physical education, post traumatic and/or post-operative rehabilitation, rhetoric training, art performance training and the like, i.e. all fields in which a real time feedback related to physical exercises and movements is beneficial and/or required.

BRIEF DESCRIPTION OF THE DRAWINGS

In the following description, detailed embodiments of a feedback device and a feedback method according to the invention are described with reference to the Figures, in which FIG. 1 diagrammatically shows a feedback device according to the invention.

DETAILED DESCRIPTION OF THE PRESENT INVENTION

Figure 1:
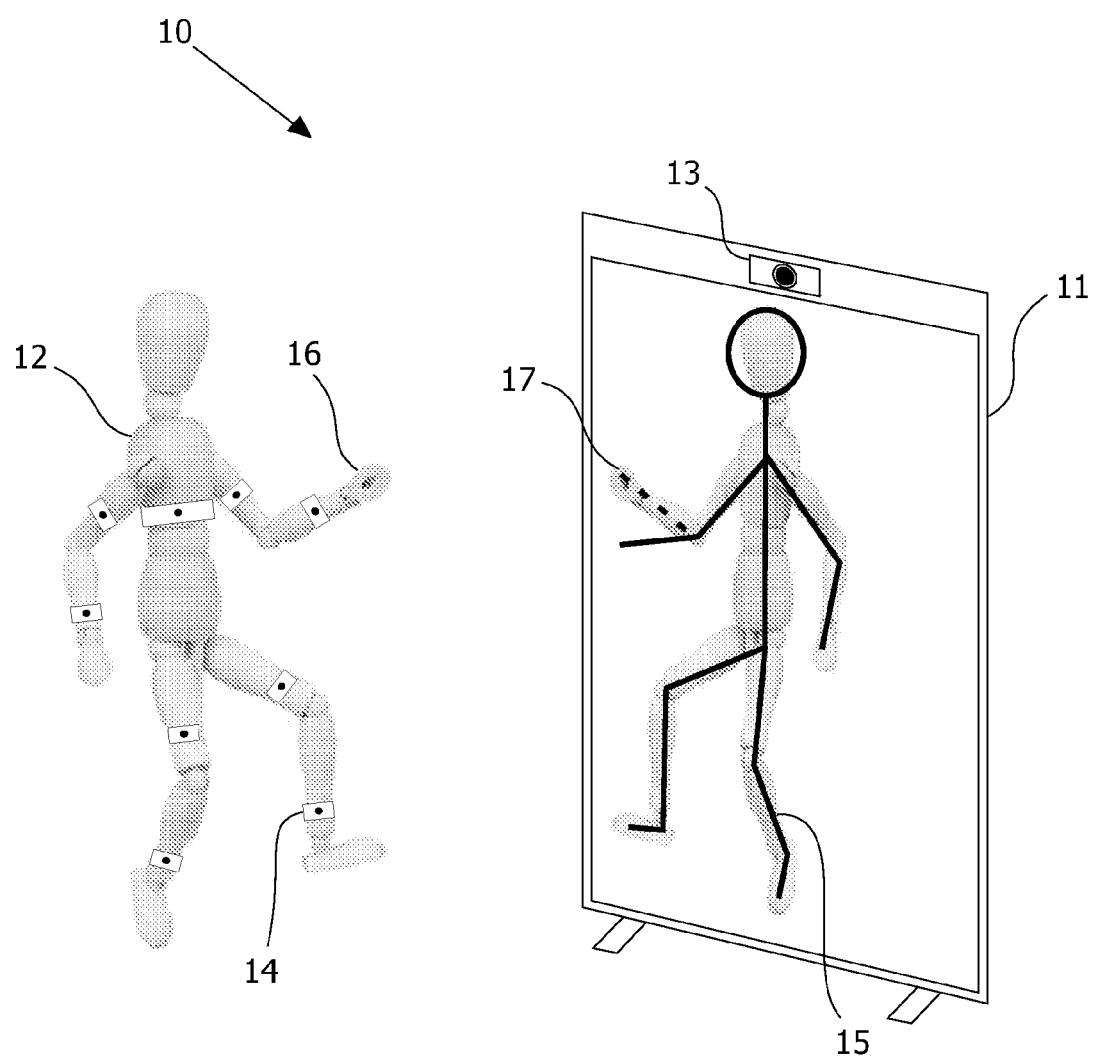

FIG. 1 shows a mirror display feedback system 10 according to the invention, comprising a mirror display 11 which consists of a wall-mounted mirror that provides the possibility to show a computer graphic on its surface. Moreover, the system comprises a camera 13, which may be stereo camera, which records the movements of a patient 12 standing in front of the mirror. The patient carries position sensors 14. A processing unit, not shown, creates an animation providing a template posture and/or movement animation 15, which is then displayed as a rendered template animation on the mirror display 11.

When the system is in use, the patient 13 sees himself in the mirror display 11 just as in any traditional mirror. Additionally, a template posture and/or movement animation 15 is overlaid in the mirror display 11, which is comparable to the patient's mirror image in size and orientation. While executing a therapy exercise, the patient 13 sees himself in the mirror, and the overlaid rendered figure performs the template posture and/or movement.

Thus the patient can directly see any discrepancies between his movements and the template posture and/or movement. As he sees himself in the mirror, and not a rendered representation, the intuitive realization of his deficiencies in exercise execution is much easier.

In FIG. 1 there is a discrepancy between the posture of the patient's left hand and the respective template posture. The patient can immediately perceive this discrepancy by comparing the computer generated animation and his own mirror image. Moreover, the CPU connected with the mirror display device detects said discrepancy and creates feedback information, which consist of a dotted line 17 in FIG. 1.

Figure 2:
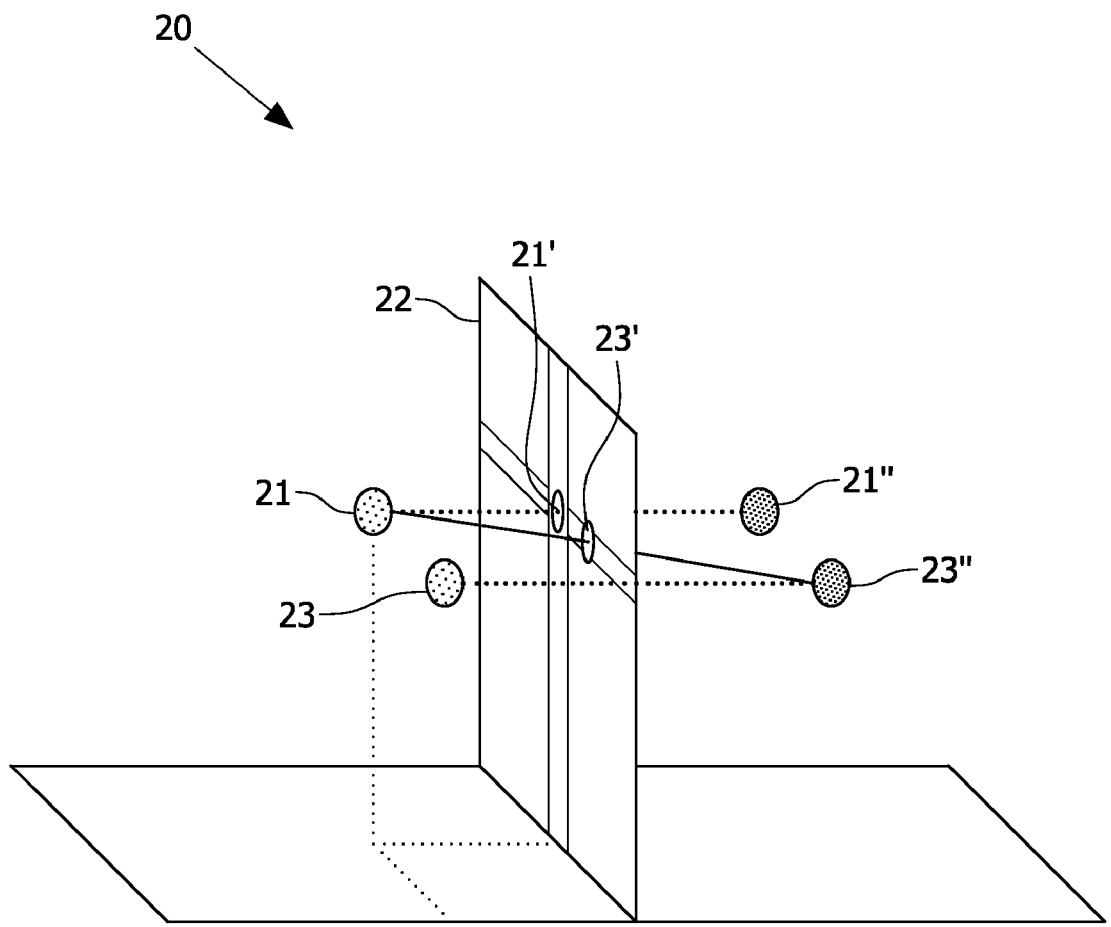
FIG. 2 diagrammatically shows a process of overlaying a mirror image with a display image in the device of FIG. 1.

In FIG. 2 the process to overlay a mirror image with a display image in mirror display feedback system 20 according to the invention is shown. The location of the eyes (21, only one eye is symbolically shown for reasons of clarity) is determined, e.g. by means of a stereo camera (not shown), coupled to an image processing module (not shown). The X,Y-pixel-coordinates of the eye (21) are calculated by orthogonal projection onto the mirror plane (22). Other options to determine the position in space include ultrasound triangulation, or use of passive or active sensors.

From the X,Y-coordinates the proper pixel location for the eyes can be derived. The location of the extremities (23, only one hand is symbolically shown for reasons of clarity) are determined, e.g. by means of a stereo camera (not shown), coupled to an image processing module (not shown). The X,Y-pixel coordinates of the extremities (23) are calculated by orthogonal projection onto the mirror plane (22), followed by scaling in the x and y direction by a factor of 0.5. As a result, a screen pixel switched on at the location 21' in the mirror plane 22 will be overlaid onto the virtual image 21" of the eyes. Likewise, a pixel switched on at the location 23' in the mirror plane 22 will be overlaid onto the virtual image of the hand 23".

By this means, the patient may consistently compare the mirrored image of his body posture with the predetermined body posture which is displayed on the mirror screen, and which indicates predetermined movements and/or postures the patient is expected to carry out in order to do rehabilitation exercises.

EXAMPLES

In the following, the present invention is demonstrated by means of examples, which by no means should be understood to limit the scope of the invention.

The user approaches the system in order to carry out an exercise for his rehabilitation. In one embodiment he is wearing colour markers on selected body positions such as wrists, elbows etc. The patient disposes himself in front of the mirror display such that he can see himself fully in the mirror. If this is the case, a stereo-camera mounted in the frame of the mirror is able to see the patient fully. A colour-tracking algorithm finds the markers in the camera images of the left and right camera of the stereo camera pair. Using calibration information of the camera system it is then possible to compute the position of the markers worn by the patient in a 3D coordinate system. This procedure is standard for stereo camera systems and can e.g. be performed by the 'Bumblebee' stereo camera manufactured by Point Grey (www.pointgrey.com), which contains a software development kit for computing 3D positions of image features. Once the 3D coordinates of the marker points are known it is a standard geometric calculation to derive the expected points of appearance of the mirror images of the markers on the surface of the mirror display. These points are subsequently used for generating a picture of a rendered figure on the mirror display in such a way that the position of the points indicated by the markers of rendered figure and mirror image coincide. This means that, while the patient is at rest at the beginning of the exercise, a rendered figure is generated that has the same size and body posture as the patient. The user sees the rendered figure perfectly overlaying his mirror image. When the exercise starts, the rendered figure is animated according to a stored template movement. The patient tries to move according to the template. He can easily see any discrepancies as his limbs and those of the rendered figure do not move synchronously. Additional feedback can be displayed on the mirror display, e.g. by colouring the background part of the display where the discrepancy of patient and template posture and/or movement is most severe.

While the invention has been illustrated and described in detail in the drawings and the foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The particular combinations of elements and features in the above detailed embodiments are exemplary only; the interchanging and substitution of these teachings with other teachings in this and other patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and equivalents thereto. Furthermore, reference signs used in the description and claims do not limit the scope of the invention as claimed.

The invention claimed is:

1. A feedback device for guiding and supervising physical exercises, comprising:
    a computer device having a processor and a memory;
    a mirror display device comprising a display device having a reflective surface; and
    position-sensing unit configured to detect a person disposed before the mirror display device,
    wherein the processor is configured to generate an animation of the person, based on data provided by the position-sensing unit, and to display said animation on the mirror display device in such a way that the displayed animation and a reflected image of the person are overlaid one on top of the other, and
    wherein the generated animation represents a template of postures.

2. The feedback device according to claim 1, further comprising a controller configured to control a transmission and a reflectance of the reflective surface.

3. The feedback device according to claim 2, wherein the mirror display comprises a polarizing film, disposed on the mirror display device, and wherein the polarizing film is configured to adjusts at least a portion of its surface so as to be either transmissive, reflective, or semi-reflective.

4. The feedback device according to claim 1, wherein the position-sensing unit comprises at least one of
    body-worn sensors or markers, and
    a camera system.

5. The feedback device according to claim 4, wherein said camera system comprises a stereo camera.

6. The feedback device of claim 1, wherein the processor is further configured to display deviations between the template and the reflected image of the person.

7. The feedback device of claim 6, wherein the displayed deviations comprise dashed lines.

8. A feedback method for guiding and supervising physical exercises, said method comprising the acts of:
    disposing a person before a feedback device comprising a processor, a memory, a mirror display device comprising a display device having a reflective surface for displaying a reflected image of the person, and a position-sensing unit for detecting the person disposed before the mirror display device;
    detecting a body posture and/or body movements of the person sensed by the position-sensing unit, and
    generating and displaying a computer-generated animation on the mirror display device overlaid one on top of the reflected image of the person, wherein the computer-generated animation represents a template of postures.

9. The feedback method according to claim 8, further comprising the act of
    detecting any deviations between the template posture and/or movement and the body posture and/or body movements of the person.

10. The feedback method according to claim 9, further comprising the act of
    generating feedback information according to said deviation.

11. The feedback method according to claim 8, further comprising the act of executing algorithms selected from the group consisting of at least one of:
    an algorithm to detect 3D positions of the person and his limbs when disposed before the mirror display device;
    an algorithm to compute coordinates of the mirror image of the person and/or his limbs on a surface of the mirror display device;
    an algorithm for creating a computer-generated image of a figure having limbs that appear at same points on the surface of the mirror display device as in the mirror image, as computed by the algorithm to compute coordinates;
    an algorithm to animate the computer-generated image according to the template posture and/or movement; and
    an algorithm to generate feedback information according to the deviation of the person's posture and/or movement from the template posture and/or movement.

12. The feedback method of claim 8, wherein further comprising the act of displaying deviations between the template and the reflected image of the person.

13. The feedback method of claim 12, wherein the displayed deviations comprise dashed lines.

* * * * *